(12) United States Patent
Ma et al.

(10) Patent No.: US 10,336,712 B2
(45) Date of Patent: Jul. 2, 2019

(54) COMPOUND FOR ENHANCING THE COUPLING DEGREE OF COMPLEX TRPV4-KCA2.3 AND ANTI-HYPERTENSION APPLICATIONS THEREOF

(71) Applicant: Jiangnan University, Wuxi (CN)

(72) Inventors: Xin Ma, Wuxi (CN); Dongxu He, Wuxi (CN); Chunlei Tang, Wuxi (CN); Peng Zhang, Wuxi (CN); Zhen Chen, Wuxi (CN); Yanfei Cai, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 15/773,553

(22) PCT Filed: May 12, 2017

(86) PCT No.: PCT/CN2017/084079
§ 371 (c)(1),
(2) Date: May 3, 2018

(87) PCT Pub. No.: WO2018/184274
PCT Pub. Date: Oct. 11, 2018

(65) Prior Publication Data
US 2019/0077769 A1    Mar. 14, 2019

(30) Foreign Application Priority Data
Apr. 7, 2017 (CN) .......................... 2017 1 02242189

(51) Int. Cl.
C07D 239/90 (2006.01)
A61P 9/12 (2006.01)
A61K 31/498 (2006.01)

(52) U.S. Cl.
CPC .......... *C07D 239/90* (2013.01); *A61K 31/498* (2013.01); *A61P 9/12* (2018.01)

(58) Field of Classification Search
CPC .................................................... C07D 239/90
See application file for complete search history.

(56) References Cited

FOREIGN PATENT DOCUMENTS

CN          101400672 A      4/2009

OTHER PUBLICATIONS

Ambinter, CAS Abstract Registry No. 1119503-63-7 (2009) (Year: 2009).*
Sun Chun-Yuan et al. "High salt diet enhances the physical coupling between TRPV4 and cPLA2", Chinese Pharmacological Bulletin Dec. 31, 2016, 32(12), pp. 1718-1723.
Kin Ma et al."Role of TRPV4-SKCa3 ion channel complex in regulation of arterial blood flow and blood pressure", Journal of Ningxia Medical University, Published on: Aug. 31, 2011, p. 181, the abstract.

* cited by examiner

*Primary Examiner* — Alexander R Pagano
(74) *Attorney, Agent, or Firm* — Gokalp Bayramoglu

(57) ABSTRACT

The applicant provides a compound for enhancing the space coupling degree of an endothelial cell ion channel complex TRPV4-KCa2.3 and anti-hypertension applications thereof. By finding the structural domains of the interacting sites of the endothelial cell ion channel complex TRPV4-KCa2.3, a compound with specificity which can act at the two interacting sites is prepared in the present invention. It is found that the compound can enhance the space coupling degree of the TRPV4-KCa2.3 complex and has great significance for the research and development of anti-hypertension drugs.

1 Claim, 3 Drawing Sheets

Specification includes a Sequence Listing.

SEQUENCE LISTING

```
<160> NUMBER OF SEQ ID NOS: 26

<210> SEQ ID NO 1
<211> LENGTH: 58
<212> TYPE: PRT
<213> ORGANISM: artificial sequence
<220> FEATURE:
<223> OTHER INFORMATION: synthesized

<400> SEQUENCE: 1

Tyr Gly Arg Lys Lys Arg Arg Gln Arg Arg Arg Thr Gly Lys Thr Cys
```

```
            1               5                    10                  15
Leu Pro Lys Ala Leu Leu Asn Leu Ser Asn Gly Arg Asn Asp Thr Ile
                    20                  25                  30

Pro Val Leu Leu Asp Ile Ala Glu Arg Thr Gly Asn Met Arg Glu Phe
            35                  40                  45

Ile Asn Ser Pro Phe Arg Asp Ile Tyr Tyr
            50                  55

<210> SEQ ID NO 2
<211> LENGTH: 28
<212> TYPE: PRT
<213> ORGANISM: artificial sequence
<220> FEATURE:
<223> OTHER INFORMATION: synthesized

<400> SEQUENCE: 2

Tyr Gly Arg Lys Lys Arg Arg Gln Arg Arg Arg Lys Leu Glu Leu
 1               5                  10                  15

Thr Lys Ala Glu Lys His Val His Asn Phe Met Met
            20                  25

<210> SEQ ID NO 3
<211> LENGTH: 29
<212> TYPE: DNA
<213> ORGANISM: artificial sequence
<220> FEATURE:
<223> OTHER INFORMATION: synthesized

<400> SEQUENCE: 3 gccaccccccc atcctcaaaa cggggaaga                                    29

<210> SEQ ID NO 4
<211> LENGTH: 29
<212> TYPE: DNA
<213> ORGANISM: artificial sequence
<220> FEATURE:
<223> OTHER INFORMATION: synthesized

<400> SEQUENCE: 4
tcttccccgt tttgaggatg gggggtggc                                     29

<210> SEQ ID NO 5
<211> LENGTH: 24
<212> TYPE: DNA
<213> ORGANISM: artificial sequence
<220> FEATURE:
<223> OTHER INFORMATION: synthesized

<400> SEQUENCE: 5
cgggagccgt cccgaggcca gaca                                          24

<210> SEQ ID NO 6
<211> LENGTH: 24
<212> TYPE: DNA
<213> ORGANISM: artificial sequence
<220> FEATURE:
<223> OTHER INFORMATION: synthesized

<400> SEQUENCE: 6
tgtctggcct cgggacggct cccg                                          24

<210> SEQ ID NO 7
<211> LENGTH: 32
<212> TYPE: DNA
```

```
<213> ORGANISM: artificial sequence
<220> FEATURE:
<223> OTHER INFORMATION: synthesized

<400> SEQUENCE: 7
cagagacatc tactactttg gggagctgcc ct                                    32

<210> SEQ ID NO 8
<211> LENGTH: 32
<212> TYPE: DNA
<213> ORGANISM: artificial sequence
<220> FEATURE:
<223> OTHER INFORMATION: synthesized

<400> SEQUENCE: 8
agggcagctc cccaaagtag tagatgtctc tg                                    32

<210> SEQ ID NO 9
<211> LENGTH: 31
<212> TYPE: DNA
<213> ORGANISM: artificial sequence
<220> FEATURE:
<223> OTHER INFORMATION: synthesized

<400> SEQUENCE: 9
gggaggctac ttctacaggg ggaacacggt g                                     31

<210> SEQ ID NO 10
<211> LENGTH: 31
<212> TYPE: DNA
<213> ORGANISM: artificial sequence
<220> FEATURE:
<223> OTHER INFORMATION: synthesized

<400> SEQUENCE: 10
caccgtgttc ccctgtaga agtagcctcc c                                      31

<210> SEQ ID NO 11
<211> LENGTH: 28
<212> TYPE: DNA
<213> ORGANISM: artificial sequence
<220> FEATURE:
<223> OTHER INFORMATION: synthesized

<400> SEQUENCE: 11
ggcgacagga ctcggatggc ctttcgcc                                         28

<210> SEQ ID NO 12
<211> LENGTH: 28
<212> TYPE: DNA
<213> ORGANISM: artificial sequence
<220> FEATURE:
<223> OTHER INFORMATION: synthesized

<400> SEQUENCE: 12
ggcgaaaggc catccgagtc ctgtcgcc                                         28

<210> SEQ ID NO 13
<211> LENGTH: 36
<212> TYPE: DNA
<213> ORGANISM: artificial sequence
<220> FEATURE:
<223> OTHER INFORMATION: synthesized

<400> SEQUENCE: 13
acctggagac agttctcaac aatgatgagg acaccc                                36
```

<210> SEQ ID NO 14
<211> LENGTH: 36
<212> TYPE: DNA
<213> ORGANISM: artificial sequence
<220> FEATURE:
<223> OTHER INFORMATION: synthesized

<400> SEQUENCE: 14
gggtgtcctc atcattgttg agaactgtct ccaggt                                36

<210> SEQ ID NO 15
<211> LENGTH: 38
<212> TYPE: DNA
<213> ORGANISM: artificial sequence
<220> FEATURE:
<223> OTHER INFORMATION: synthesized

<400> SEQUENCE: 15
ctaccagtac tatggcttcg agctgaacaa gaactcaa                              38

<210> SEQ ID NO 16
<211> LENGTH: 38
<212> TYPE: DNA
<213> ORGANISM: artificial sequence
<220> FEATURE:
<223> OTHER INFORMATION: synthesized

<400> SEQUENCE: 16
ttgagttctt gttcagctcg aagccatagt actggtag                              38

<210> SEQ ID NO 17
<211> LENGTH: 33
<212> TYPE: DNA
<213> ORGANISM: artificial sequence
<220> FEATURE:
<223> OTHER INFORMATION: synthesized

<400> SEQUENCE: 17
tggtgagctg agtgtcaacc acagctacca caa                                   33

<210> SEQ ID NO 18
<211> LENGTH: 42
<212> TYPE: DNA
<213> ORGANISM: artificial sequence
<220> FEATURE:
<223> OTHER INFORMATION: synthesized

<400> SEQUENCE: 18
catgtgcaca acttcatgat gctaaagaag attgaccatg cc                         42

<210> SEQ ID NO 19
<211> LENGTH: 42
<212> TYPE: DNA
<213> ORGANISM: artificial sequence
<220> FEATURE:
<223> OTHER INFORMATION: synthesized

<400> SEQUENCE: 19
ggcatggtca atcttcttta gcatcatgaa gttgtgcaca tg                         42

<210> SEQ ID NO 20
<211> LENGTH: 44
<212> TYPE: DNA
<213> ORGANISM: artificial sequence
<220> FEATURE:

<223> OTHER INFORMATION: synthesized

<400> SEQUENCE: 20
gctccgtgat taagtcatac atgtcaatct tctttagcag cttt					44

<210> SEQ ID NO 21
<211> LENGTH: 42
<212> TYPE: DNA
<213> ORGANISM: artificial sequence
<220> FEATURE:
<223> OTHER INFORMATION: synthesized

<400> SEQUENCE: 21
gtctataaac atacaaagct gcatgccaaa gtcaggaaac ac					42

<210> SEQ ID NO 22
<211> LENGTH: 42
<212> TYPE: DNA
<213> ORGANISM: artificial sequence
<220> FEATURE:
<223> OTHER INFORMATION: synthesized

<400> SEQUENCE: 22
gtgtttcctg actttggcat gcagctttgt atgtttatag ac					42

<210> SEQ ID NO 23
<211> LENGTH: 44
<212> TYPE: DNA
<213> ORGANISM: artificial sequence
<220> FEATURE:
<223> OTHER INFORMATION: synthesized

<400> SEQUENCE: 23
aaagctgcta agaagattg acatgtatga cttaatcacg gagc					44

<210> SEQ ID NO 24
<211> LENGTH: 44
<212> TYPE: DNA
<213> ORGANISM: artificial sequence
<220> FEATURE:
<223> OTHER INFORMATION: synthesized

<400> SEQUENCE: 24
gctccgtgat taagtcatac atgtcaatct tctttagcag cttt					44

<210> SEQ ID NO 25
<211> LENGTH: 42
<212> TYPE: DNA
<213> ORGANISM: artificial sequence
<220> FEATURE:
<223> OTHER INFORMATION: synthesized

<400> SEQUENCE: 25
ctccgtgatt aagtcataca tcatcatgaa gttgtgcaca tg					42

<210> SEQ ID NO 26
<211> LENGTH: 42
<212> TYPE: DNA
<213> ORGANISM: artificial sequence
<220> FEATURE:
<223> OTHER INFORMATION: synthesized

<400> SEQUENCE: 26
catgtgcaca acttcatgat gatgtatgac ttaatcacgg ag					42

COMPOUND FOR ENHANCING THE COUPLING DEGREE OF COMPLEX TRPV4-KCA2.3 AND ANTI-HYPERTENSION APPLICATIONS THEREOF

CROSS REFERENCE TO RELATED APPLICATIONS

This application is the national phase entry of International Application PCT/CN2017/084079, filed on May 12, 2017 which is based upon and claims priority to Chinese Patent Application No. CN2017102242189, filed on Apr. 7, 2017 the entire contents of which are incorporated herein by reference.

TECHNICAL FIELD

The present invention relates to the technical field of anti-hypertension drugs, in particular to an application of a compound for enhancing the space coupling degree of an endothelial cell ion channel complex TRPV4-KCa2.3 in the inhibition of hypertension.

BACKGROUND

Hypertension is a lifelong disease, and patients with such disease need to take medicine every day of their life, according to the Study Report on Operation Surveillance and Development Prospects of the Chinese Anti-hypertension Drugs Market from 2014 to 2019 issued by the China Industrial Information Network. The development of anti-hypertension drugs has gone through decades. Diuretics were launched in the 1960s; β-receptor antagonists were launched in the 1970s; calcium channel blockers and angiotensin-converting enzyme inhibitors (ACEI) were pushed out in the 1980s; angiotensin II receptor antagonists (Chatain) with specificity were developed in the 1990s; and successively, a plurality of prescribed preparations and compound preparations were approved by the American FDA to be launched on the market, becoming the first choices of hypertension treatment.

The prescribed anti-hypertension drugs are relatively maturely developed, and according to their mechanisms, can be basically classified into the following five types.
  (1) Diuretics: hydrochlorothiazide, bumetanide, indapamide, diuretic compound preparations, etc.;
  (2) Calcium channel blockers: nifedipine, amlodipine, diltiazem, verapamil, etc.;
  (3) β-receptor antagonists: propranolol, atenolol, metoprolol, labetalol, etc.;
  (4) Angiotensin-converting enzyme inhibitors: captopril, enalapril, benazepril, lisinopril, etc.;
  (5) Angiotensin II receptor antagonists: losartan, valsartan, telmisartan, olmesartan, etc.

The anti-hypertension drugs of different mechanisms act at different target points, and have respective advantages. During hypertension treatment, the drugs applicable to a patient are selected. The majority of the patients are usually treated with a combination method after it is proved that a single drug fails to achieve the treatment effects.

Transient receptor potential vanilloid 4 (TRPV4) is a member of the TRP, and is a non-selective cation channel. The TRPV4 channel has six transmembrane α-coiled coil domains, respectively S1-S6, has a pore ring domain through which ions are adjusted to move between S5 and S6, and has a terminal N and a terminal C both located in a cell. The TRPV4 channel must form a functional homotetramer or heterotetramer to take effect in signal transduction. The terminal N of the TRPV4 channel includes at least three ankyrin binding sites. The ankyrin can interact with the TRPV4 channel, and can inhibit the receptor IP3 so as to adjust the release of $Ca^{2+}$ in cells. The TRPV4 channel has very high $Ca^{2+}$ permeability, is massively expressed in vascular endothelial cells, and as a $Ca^{2+}$ channel, participates in the signal transduction of the endothelial cells.

Small conductance Ca2+-activated K+ channels SKca are mainly classified into three types, KCa2.1, KCa2.2 and KCa2.3, where KCa2.3 is mainly expressed and distributed in nerve cells, colloid cells, smooth vascular muscle cells and endothelial cells. KCa2.3 plays an important role in the physiological activities of the human body, in particular in the relaxation process of smooth muscles. The continuous activation of KCa2.3 results in continuous hyperpolarization of the membrane potential in the vascular endothelial cells, and the hyperpolarization signal reaches the smooth muscles nearby. Blocking or inhibiting KCa2.3 greatly increases the vascular resistance, generates peripheral arterial resistance, and enhances blood pressure.

Research shows that TRPV4 and KCa2.3S perform physical interaction with each other on the vascular endothelial cells. $Ca^{2+}$ enters the cells via the TPR channels to activate the potassium ion channels and then to cause vasodilatation. However, the specific interacting site is still unknown. Searching for the interacting site and finding a compound which works at the site has great significance for the research and development of anti-hypertension drugs.

SUMMARY

Aiming at the above problems in the prior art, the applicant provides a compound for enhancing the space coupling degree of an endothelial cell ion channel complex TRPV4-KCa2.3 and applications thereof in the inhibition of hypertension. By finding structural domains of the interacting sites of the endothelial cell ion channel complex TRPV4-KCa2.3, a compound with specificity which can act at the two interacting sites is prepared in the present invention. It is found that the compound can enhance the space coupling degree of the complex TRPV4-KCa2.3 and has great significance for the research and development of anti-hypertension drugs.

The technical solution of the present invention is as follows.

The applicant provides a compound or a pharmaceutically acceptable salt thereof for enhancing the space coupling degree of an endothelial cell ion channel complex TRPV4-KCa2.3. The structural domains of the interacting sites of the endothelial cell ion channel complex TRPV4-KCa2.3 are the structural domain AR2 of the protein TRPV4 and the structural domain 17C of the protein KCa2.3. The compound is a compound as shown in formula (1), or a pharmaceutically acceptable salt thereof. The serial number of the compound is JNc-440:

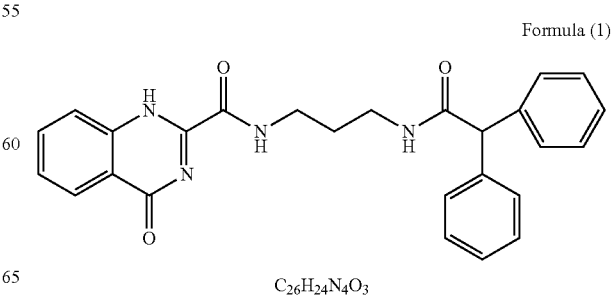

Formula (1)

$C_{26}H_{24}N_4O_3$

A preparation method of the compound for enhancing the space coupling degree of an endothelial cell ion channel complex TRPV4-KCa2.3 specifically includes the following steps:

(1) providing propane diamine with t-butyloxycarboryl to protect a single amino first:

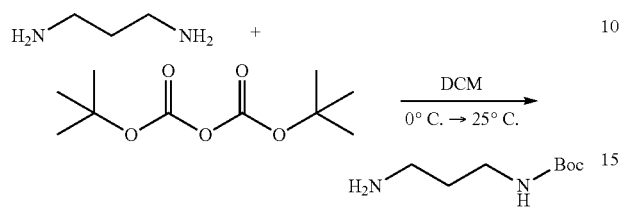

(2) another exposed amino reacting with diphenylacetyl chloride to generate amide:

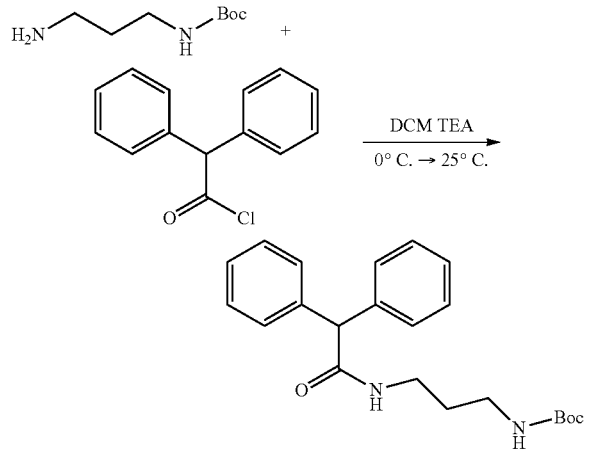

(3) removing t-butyloxycarboryl protection from the amide under acidic conditions:

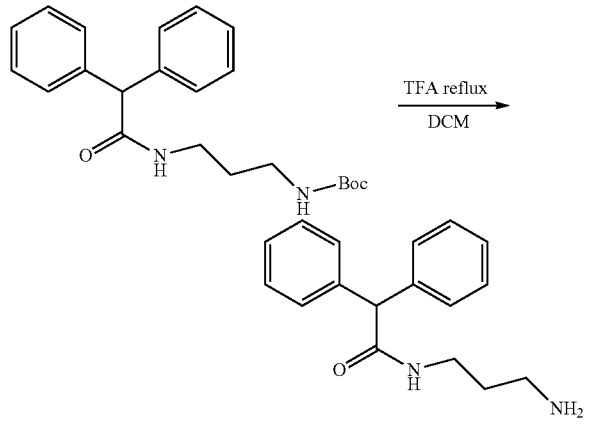

(4) the compound obtained after removing the t-butyloxycarboryl protection performing amino-ester exchange with 4-quinazolone-2-carboxylic acid ethyl ester to obtain a target compound:

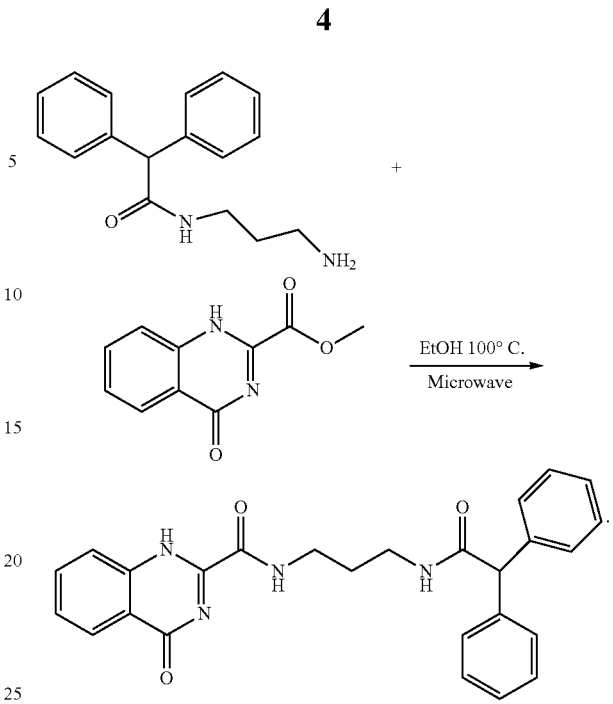

The applicant also provides an application of the compound. The compound can act on the structural domains of the interacting sites of the TRPV4 and KCa2.3, thus enhancing the space coupling degree of the complex TRPV4-KCa2.3.

The applicant also provides another application of the compound. The compound can inhibit hypertension.

The applicant also provides an application of the structural domain AR2 of the protein TRPV4 and the structural domain 17C of the protein KCa2.3 of the interacting sites of the endothelial cell ion channel complex TRPV4-KCa2.3 in the inhibition of hypertension.

The present invention has the following technical effects:

First, in the present invention, the structural domains of the interacting sites of the protein TRPV4 and the protein KCa2.3 are found by the method of structural domain site mutation; then, a compound capable of enhancing the space coupling degree of the complex TRPV4-KCa2.3 is screened, and a new method for preparing the compound is researched and developed; and finally, the compound acts on mice with hypertension to test the hypertension treatment effect.

Through study, the inventor found the mutual interacting sites of the structural domain AR2 of the TRPV4 and the structural domain 17C of KCa2.3, and prepared the compound which acts at the two interacting sites at the same time. Through the results obtained after the compound was applied to mice with hypertension, it was found that the compound can enhance the space coupling degree of the complex TRPV4-KCa2.3 to achieve the effect of inhibiting hypertension. The invention has great significance for the research and development of anti-hypertension drugs.

DETAILED DESCRIPTION

Figure 1:
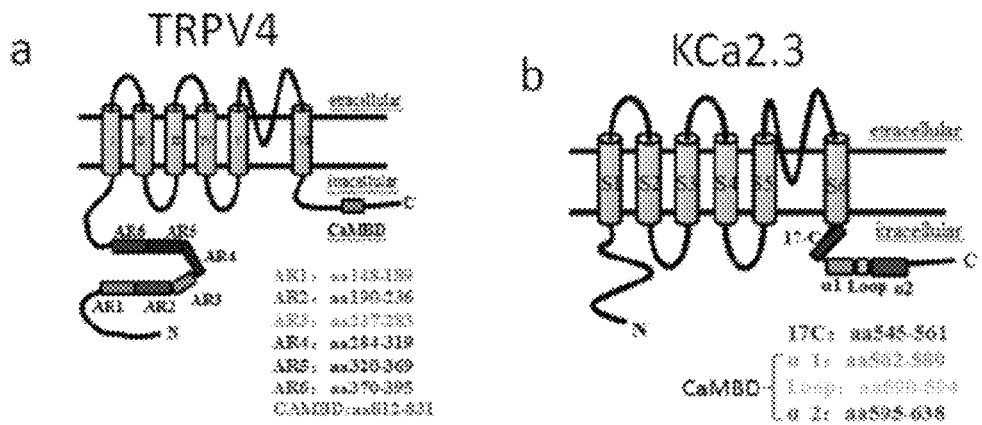
FIG. 1 is a schematic diagram of the three-dimensional structures and functional zones of the protein TRPV4 and the protein KCa2.3.

The present invention is described in further detail with reference to the attached drawings and embodiments.

Experimental materials of the following embodiments are as follows:

Cell system: HEK293 cells, purchased from the Shanghai Cell Bank of the Chinese Academy of Sciences.

Experimental animals: C57BL/6 J male mice, 8 weeks aged, SPF grade, purchased from Changzhou Cavens Experimental Animal Co., Ltd.

Plasmids and primers: Plasmid templates containing whole-genome CFP-TRPV4 or whole-genome YFP-KCa2.3 donated by the K S Lo College of the Chinese University of Hong Kong; primers all purchased from Sangon Biotech (Shanghai) Co., Ltd.

Oligopeptide:

AR2:
YGRKKRRQRRRTGKTCLPKALLNLSNGRNDTIPVLLDIAERTGNMREFINS

PFRDIYY;

17C:
YGRKKRRQRRRRKLELTKAEKHVHNFMM all purchased from Sangon Biotech (Shanghai) Co., Ltd.

Reagents: primary antibody goat anti-TRPV4 (sc-47527), purchased from Santa Cruz; primary antibody rabbit anti-KCa2.3 (APC-025), purchased from Alomone; secondary antibody Alexa Fluor 647 and Alexa Fluor 488, purchased from Invitrogen.

Point mutation kit QuickChange™ purchased from Stratagene; DNA product purification kit and plasmid extraction kit, both purchased from Tiangen Biotech (Beijing) Co., Ltd.; DH5α competent cells, purchased from Tiangen Biotech (Beijing) Co., Ltd.

The synthesis procedures of the biotinylated JNc-440 are as follows:

(1) The compound JNc-440 is treated with phosphorus oxychloride to generate a carbonyl chloride:

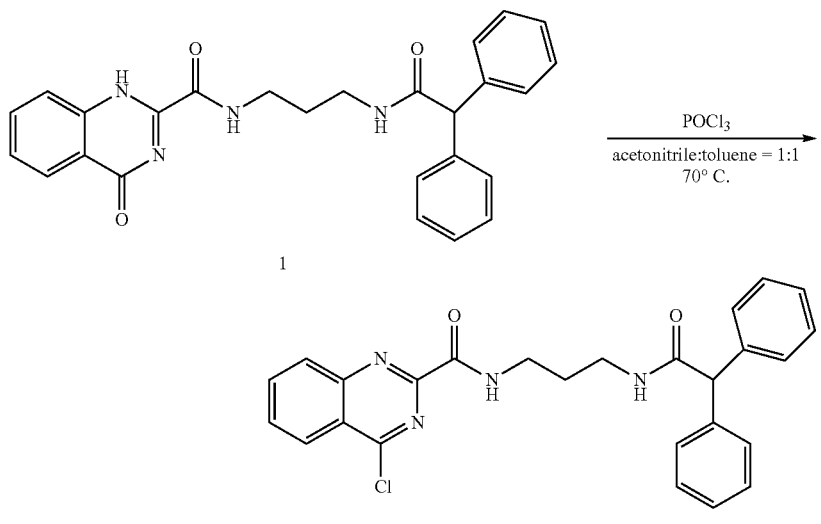

(2) The chloride and 5-amino-1-pentanol perform nucleophilic substitution:

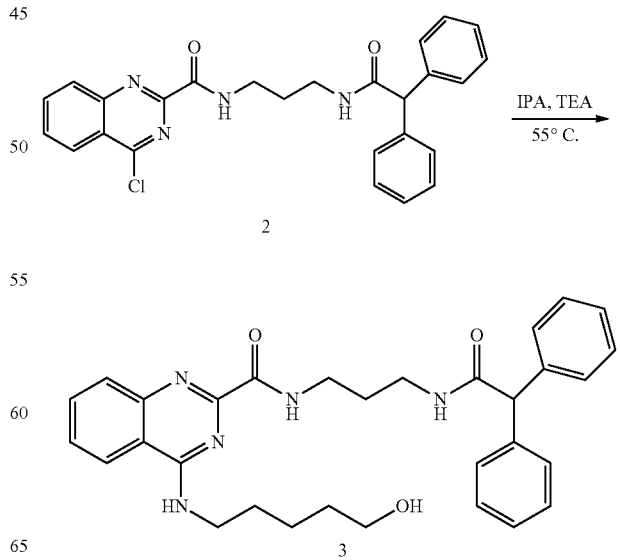

(3) Biotin and the product obtained in the previous step perform an esterification reaction to obtain biotinylated JNc-440:

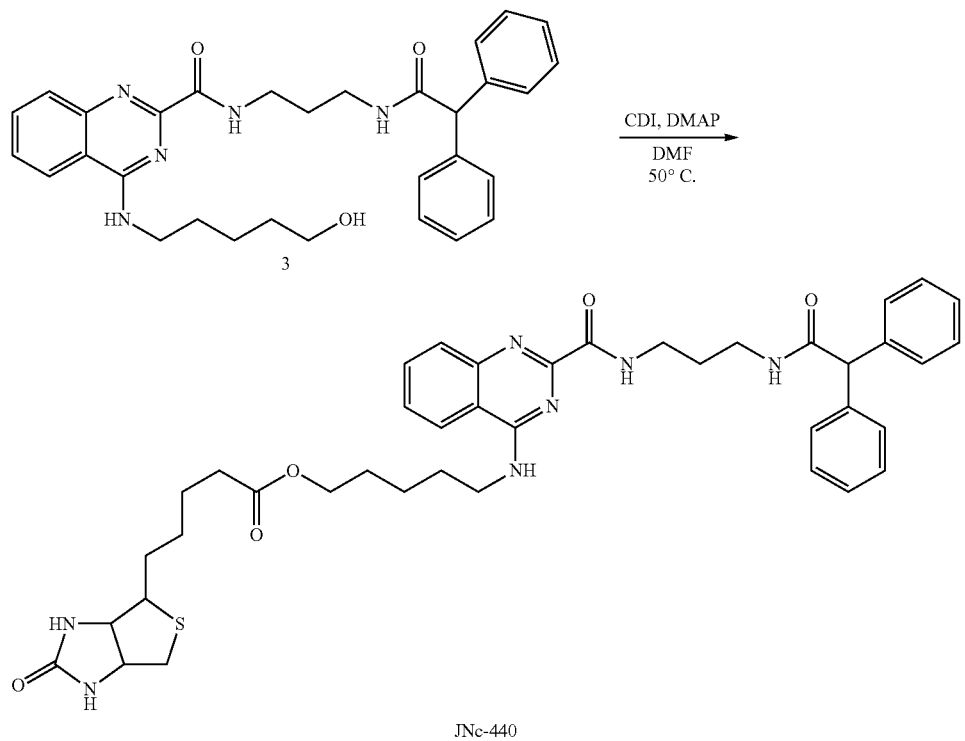

JNc-440

8% High-salt feed (TP6032-S8), purchased from Trophic Animal Feed High-tech Co., Ltd; L-NAME (Nitro-L-arginine) (N5501-5G), purchased from Sigma; Angiotensin 2 (ANG-2) (A107852), purchased from Shanghai Aladdin Bio-Chem Technology Co., Ltd;

All other reagents were purchased from Sinopharm Chemical Reagent Co., Ltd.

Experimental instruments: blood pressure gauge for rats and mice (BP98A), purchased from SINSI; OSMOTIC PUMPS (implantable capsule osmotic pump), purchased from ALZET; gel imaging system, purchased from GENE; laser scanning confocal microscope, purchased from Leica.

Embodiment 1: Preparation Method of the Compound (1) A compound 1-diamine propylene (30 g, 405 mmol, 1 eq) is dissolved in 150 mL of dichloromethane, ice bathed and stirred; 2-tertiary butyl sodium bicarbonate (16.1 g, 73 mmol, 0.18 eq) is dissolved and diluted in 50 mL of dichloromethane; the mixture is poured into a flask slowly and stirred for 3 h at room temperature; after the materials react completely, detection is carried out by using thin layer chromatography (TLC), diluted with 50 mL of dichloromethane, washed with water several times, washed with saturated NaCl solution, and then dried with hydrous $Na_2SO_4$; the obtained product is concentrated to obtain a compound 2 (19 g, 27%);

(2) The compound 2 (10 g, 57 mmol, 1 eq) and triethylamine (TEA) (8.7 g, 86 mmol, 1.5 eq) are dissolved in 100 mL of dichloromethane, ice bathed and stirred; diphenylacetyl chloride (13.1 g, 57 mmol, 1 eq) is dissolved in 30 mL of dichloromethane, the mixed materials are slowly poured into a flask, and stirred for 2.5 h at room temperature; after the materials react completely, TLC detection is carried out, followed by concentration of the crude product; the concentrated product is separated with column chromatography (dichloromethane/methanol 20:1) to obtain a compound 3 (13.2 g, 63%);

(3) The compound 3 (8 g, 22 mmol, 1 eq) is dissolved in a mixed solvent (40 mL:dichloromethane:trifluoroacetic acid=4:1); the mixture is oil bathed, heated until the temperature reaches 35° C., maintained at the temperature for 1 h; after the materials react completely, TLC detection is carried out; ammonia water is added to adjust the pH value of the system to 8-9 until solid precipitates are generated; the precipitates are filtered and dried to obtain a compound 4 (5.3 g, 90%);

(4) The compound 4 (2 g, 7 mmol, 2 eq) and 4-quinazolinone-2-ethyl formate (0.8 g, 3.5 mmol, 1 eq) are dissolved in 6 mL of ethanol; the mixed materials react for 45 min at a temperature of 100° C. in a microwave reactor; after the materials react completely, TLC detection is carried out; the solution is naturally cooled to obtain white solid precipitates, and the precipitates are filtered and dried to obtain a compound 5. The compound 5 is the compound for hypertension treatment in the present invention.

Embodiment 2: Find the Structural Domains of the Interacting Sites of the Protein TRPV4 and the Protein KCa2.3

Experimental method: Possible binding sites (as shown in FIG. 1) are selected according to the three-dimensional structures and functional characteristics of the protein TRPV4 and the protein KCa2.3. The selected structural domains are mainly used to adjust the protein-protein relation, and are platforms where the proteins interact with each other. The selected binding sites are mutated such that the binding sites are lost. The used primers can be seen in Table 1.

TABLE 1

| Gene name | Primer sequence |
|---|---|
| TRPV4ΔAR1 | 5'-gccaccccccatcctcaaaacggggaaga-3'<br>5'-tcttccccgttttgaggatgggggtggc-3' |
| TRPV4ΔAR2 | 5'-cgggagccgtcccgaggccagaca-3'<br>5'-tgtctggcctcgggacggctcccg-3' |
| TRPV4ΔAR3 | 5'-cagagacatctactactttggggagctgccct-3'<br>5'-agggcagctccccaaagtagtagatgtctctg-3' |
| TRPV4ΔAR4 | 5'-gggaggctacttctacaggggaacacggtg-3'<br>5'-caccgtgttcccctgtagaagtagcctccc-3' |
| TRPV4ΔAR5 | 5'-ggcgacaggactcggatggcctttcgcc-3'<br>5'-ggcgaaaggccatccgagtcctgtcgcc-3' |
| TRPV4ΔAR6 | 5'-acctggagacagttctcaacaatgatgaggacaccc-3'<br>5'-gggtgtcctcatcattgttgagaactgtctccaggt-3' |
| TRPV4ΔCaMBD | 5'-ctaccagtactatggcttcgagctgaacaagaactcaa-3'<br>5'-ttgagttcttgttcagctcgaagccatagtactggtag-3' |
| KCa$_{2.3}$Δ17c | 5'-tggtgagctgagtgtcaaccacagctaccacaa-3'<br>5'-catgtgcacaacttcatgatgctaaagaagattgaccatgcc-3' |
| KCa$_{2.3}$Δα1 | 5'-ggcatggtcaatcttctttagcatcatgaagttgtgcacatg-3'<br>5'-gctccgtgattaagtcatacatgtcaatcttctttagcagcttt-3' |
| Kca$_{2.3}$Δloop | 5'-gtctataaacatacaaagctgcatgccaaagtcaggaaacac-3'<br>5'-gtgtttcctgactttggcatgcagctttgtatgtttatagac-3' |
| KCa$_{2.3}$Δα2 | 5'-aaagctgctaaagaagattgacatgtatgacttaatcacggagc-3'<br>5'-gctccgtgattaagtcatacatgtcaatcttctttagcagcttt-3' |
| KCa$_{2.3}$ΔCaMBD | 5'-ctccgtgattaagtcatacatcatcatgaagttgtgcacatg-3'<br>5'-catgtgcacaacttcatgatgatgtatgacttaatcacggag-3' |

The used PCR reaction system is as follows: 0.5 µl template (whole-genome CFP-TRPV4 or whole-genome YFP-KCa2.3), 25 µl Prim Star HS, upstream and downstream primers, each 0.5 µl, and H$_2$O added to 50 µl. PCR reaction process: 2 min predegeneration at a temperature of 95° C., 30 s degeneration at a temperature of 95° C., 30 s annealing at a temperature of 55° C., 5 min extension at a temperature of 68° C., 30 circulations, 10 min full extension at a temperature of 68° C. After the PCR ends, the obtained product is purified with a PCR product purification kit; the purified product is digested with the enzyme DpnI. The digestion system includes 0.4 µl enzyme DpnI, 5 µl PCR purified product, 2 µl 10× buffer, and 12.6 µl ddH2O. The digestion is carried out for 1 h at a temperature of 37° C., and deactivation is carried out for 20 min at a temperature of 80° C. The digestion product is converted into competent DH5a cells. Screened monoclone cells undergo expanding culture and then plasmids are extracted using a plasmid extraction kit. Samples are sent to test the gene sequence.

The mutated plasmids are transferred into the HEK293 cells. After transfection, the cells are laid onto a confocal vessel. After 24 h, the coupling of the two proteins before and after the mutation is detected using a laser scanning confocal microscope in FRET AB mode.

Plasmids TRPV4-ΔAR2H and plasmids KCa2.3Δ17C are constructed by the above mentioned gene mutation method, and then transferred into the HEK293 cells. After 24 h, the cells are immobilized with the PBS solution which contains 3% paraformaldehyde and 0.1% glutaraldehyde, and then washed with 0.1% sodium borohydride which is diluted with PBS. Cells undergo confining and osmosis treatment in a confining liquid (3% BSA and 0.2% Triton X-100 added into the PBS), incubated with the primary antibody at a temperature of 4 DEGC for a whole night, washed three times, and then incubated with a secondary antibody at room temperature for 45 min. Goat anti-TRPV4 and rabbit anti-KCa2.3 are used as the primary antibody, while Alexa Fluor 647 and Alexa Fluor 488 are used as the secondary antibody. At the same time, the two proteins are co-located by using stochastic optical reconstruction microscopy (STORM) to further verify the accuracy of the FRET results. Samples are prepared using the above method. Approximately 4 µL imaging buffer is added into the center of a clean confocal vessel. The buffer contains 5% (w/v) glucose, 100 mM aminothiopropionic acid, 0.8 mg/mL notatin and 40 µg/mL catalase, and is dissolved in Tris-HCL with a pH value of 7.5 or 8. The STORM imaging buffer represents spectral-resolved unimolecule image.

Figure 2:
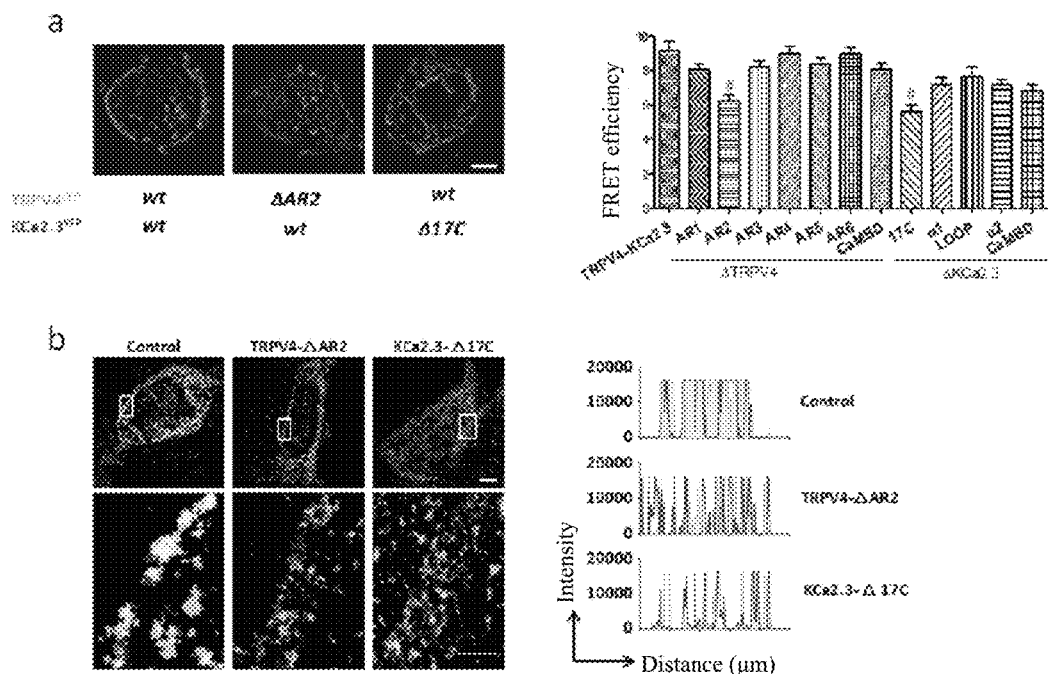
FIG. 2 is a diagram of results of finding the interacting sites of the protein TRPV4 and the protein KCa2.3 by using fluorescence resonance energy transfer and stochastic optical reconstruction microscopy in Embodiment 2 of the present invention.

Experimental results: FIG. 2a shows, compared with other mutation sites, the FRET phenomenon is obviously reduced in the structural domain AR2 where the TRPV4 is mutated or in the structural domain 17C where KCa2.3 is mutated. FIG. 2b shows further verification of the ultra-high-definition imaging experiment. According to the verification result, the structural domain AR2 of the TRPV4 and the structural domain 17C of the KCa2.3 are binding sites where two proteins are bound.

In FIG. 2a, the colors, blue-green-yellow-red, represent that the FRET efficiency increases in turn.

In FIG. 2b, red represents the protein TRPV4, green the protein KCa2.3, and yellow is the superimposing of both green and red.

Embodiment 3: The Compound Prepared in Embodiment 1 Takes the Structural Domain AR2 of the TRPV4 and the Structural Domain 17C of KCa2.3 as Target Points Experimental Method:

The endothelial cells of C57BL/6 J mouse mesentery are primarily isolated, and then incubated in a constant-temperature cell incubator. Biotinylated JNc-440 (10 μM/L) is added or oligopeptide and biotinylated JNc-440 (10 μM/L) are added into the incubator to jointly incubated with the cells for 96 h. RIPA Lysis is carried out to obtain cellular protein. The protein supernatant is added with 10 μL streptavidin magnetic beads, and the mixture is incubated at a temperature of 4° C. for a whole night. Suspension generated after the incubation is absorbed using a magnetic stand to obtain an avidin magnetic bead-biotinylated JNc-440-protein complex. The complex is suspended with 50 μL of 1× Loading buffer, and boiled for 5 min in a boiling bath. Samples are separated through SDS-PAGE. Proteins are transferred onto a PVDF membrane. The PVDF membrane with the proteins are confined in 5% BSA for 4 h at room temperature, then incubated with a primary antibody at a temperature of 4° C. for a whole night, and next incubated with a secondary antibody for 2 h at room temperature. ECL color developing agent is added. A protein imaging system is used to detect and analyze the obtained product.

Figure 3:
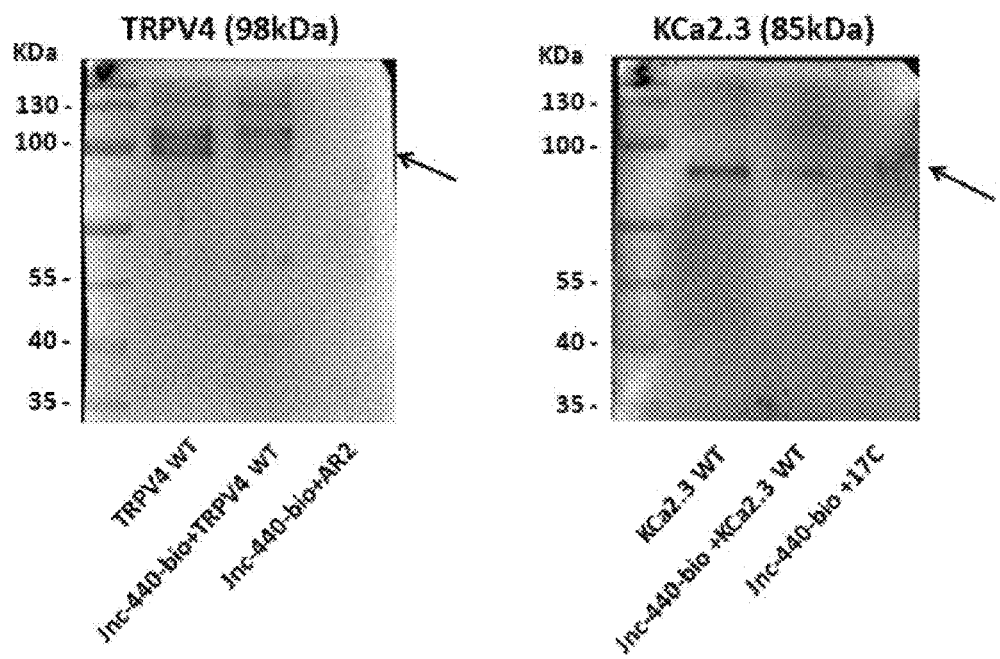
FIG. 3 is a diagram of the results of preparing a compound with a dual-target co-immunoprecipitation effect in Embodiment 1.

Experimental Results:

Experimental results can be seen in FIG. 3. The biotinylated JNc-440 can be bound with the proteins TrpV4 and KCa2.3; after the oligopeptide AR2 is added, the biotinylated JNc-440 is obviously reduced in the capability of binding with the protein TRPV4. On the other hand, compared with the reference control, after the oligopeptide 17C is added, the biotinylated JNc-440 is obviously reduced in the capability of binding with the protein KCa2.3. Results show that the biotinylated JNc-44 can be bound with TRPV4 and KCa2.3, and the binding zones are AR2 and 17C.

Embodiment 4: The Compound Prepared in Embodiment 1 can Enhance the Space Coupling Degree of the Endothelial Cell Ion Channel Complex TRPV4-KCa2.3

Experimental Method:

C57BL/6J Male mice, 8 weeks aged, are selected, and freely fed for one week. Then, the mice are classified into four groups, respectively 8% high-salt group, L-NAME group, ANG-2 group and reference group. The basic blood pressures of the four groups of mice are measured first to determine the base line of the blood pressure of the mice. The conditions of the reference group are not changed, and the blood pressure is measured every day. The high-salt group is fed with 8% high-salt feed, and then the blood pressure is measured every day. The L-name group is fed with 5% L-NAME solution, and then the blood pressure is measured every day. The ANG-2 group is injected with 4% chloral hydrate to perform anesthesia; then, the mice are respectively operated by implanting a pump on the back, wherein each pump is injected with 200 ul of 2.88 mg/ml ANG-2 solution; then, the mice are sutured and allowed to recover; after approximately 3 days, the measurement of the blood pressure begins, and then continues for about 4 weeks. The blood pressure of the high-salt group is stabilized at 120 mmHg; the blood pressures of the L-NAME and the ANG-2 group are stabilized at approximately 130 mmHg. When the blood pressure is maintained for approximately one week without rising, this represents that the modeling has succeeded.

The mesentery endothelial cells of the mice in the high blood pressure model are primarily isolated and incubated in a constant-temperature cell incubator. JNc-440 (10 μM) is added to be jointly incubated with cells for 96 h. The cells are dyed using the immunostaining method as described in Embodiment 2. Then, the coupling of the two proteins before and after the mutation is detected using the laser scanning confocal microscope in the FRET AB mode.

Figure 4:
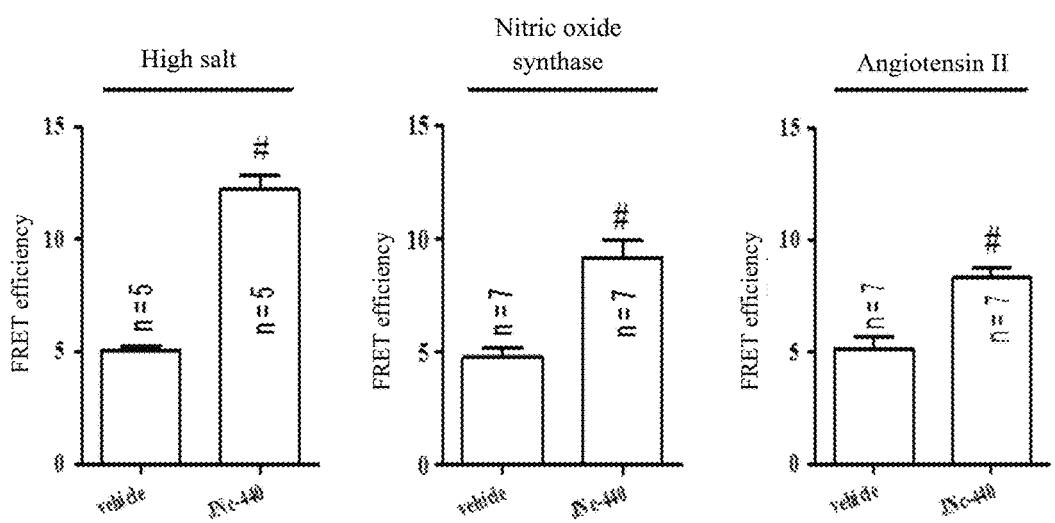
FIG. 4 is a diagram of the variation of the coupling degrees of the complex TRPV4-KCa2.3 detected using the fluorescence resonance energy transfer technology after the compound prepared in Embodiment 1 acts on mice with hypertension in Embodiment 3.

Experimental results: as shown in FIG. 4, the space coupling degree of the proteins TRPV4 and KCa2.3 is increased obviously after the compound acts on the endothelial cells of the three different high blood pressure types of mice models. This represents that the compound can enhance the space coupling degree of the ion channel complex TRPV4-KCa2.3.

Embodiment 5: Effects of the Compound Prepared in Embodiment 1 on Three High Blood Pressure Types of Mice Models Experimental method: three high blood pressure types of mice models are constructed according to the method in Embodiment 4. After modeling succeeds, JNc-440 (1 mg/kg) is injected via the caudal veins, and then the blood pressure of the mice is measured and observed.

Figure 5:
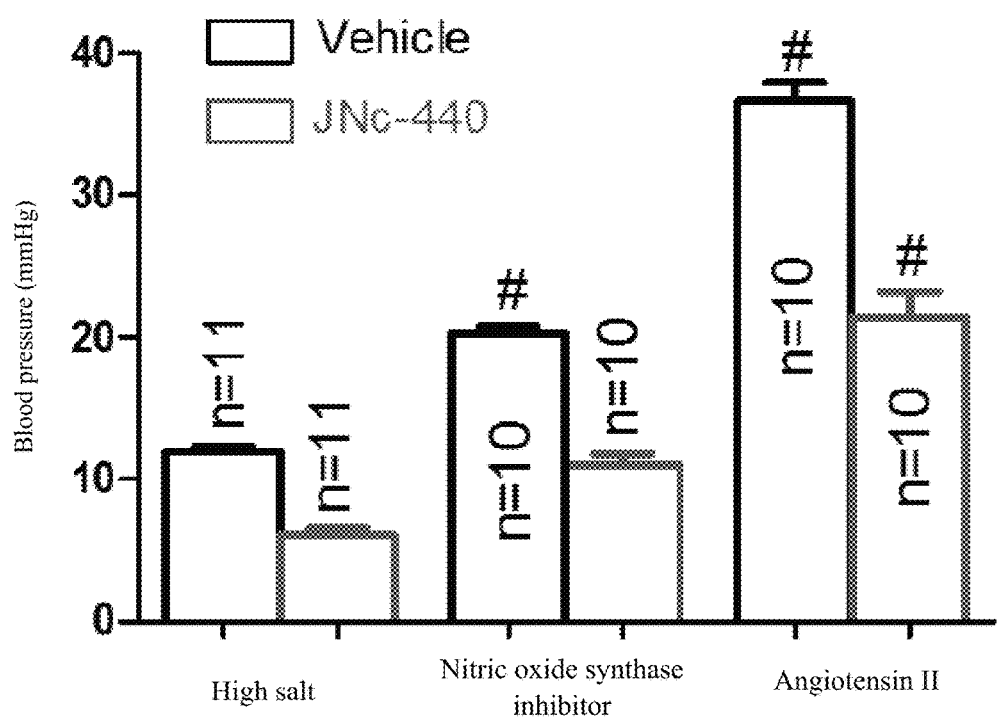
FIG. 5 is a diagram of the variation of the blood pressure detected after the compound prepared in Embodiment 1 acts on three types of mice with hypertension.

Experimental results: As shown in FIG. 5, the blood pressure of the mice drops obviously after the compound acts on the three high blood pressure types of mice models, which represents that the compound has an obvious antihypertension effect.

What is claimed is:

1. A preparation method of a compound for enhancing the space coupling degree of an endothelial cell ion channel complex TRPV4-KCa2.3, wherein structural domains of interacting sites of the endothelial cell ion channel complex TRPV4-KCa2.3 are structural domain AR2 of protein TRPV4 and structural domain 17C of protein KCa2.3 and the compound is represented by structure formula (1):

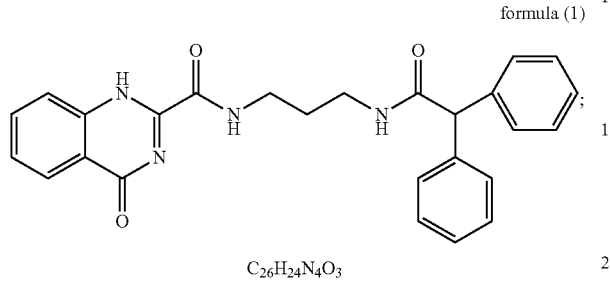

formula (1)

$C_{26}H_{24}N_4O_3$ the method comprising:
providing propane diamine with t-butyloxycarboryl to protect a single amino first:

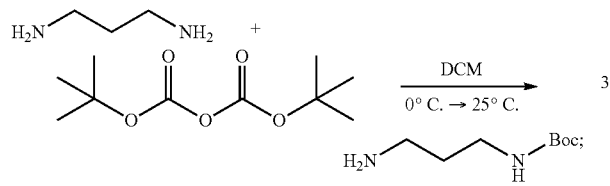

an exposed amino reacting with diphenylacetyl chloride to generate an amide:

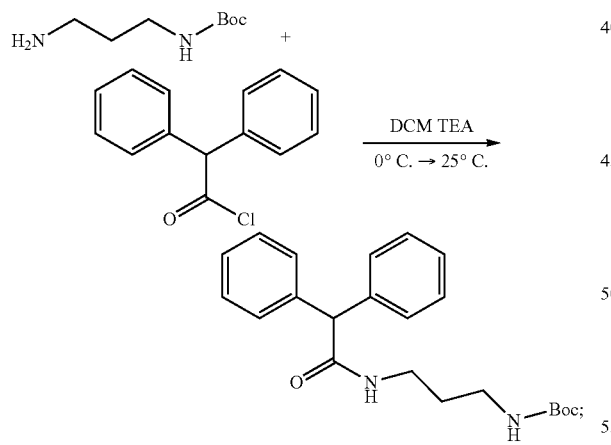

removing a t-butyloxycarboryl protection from the amide under an acidic condition:

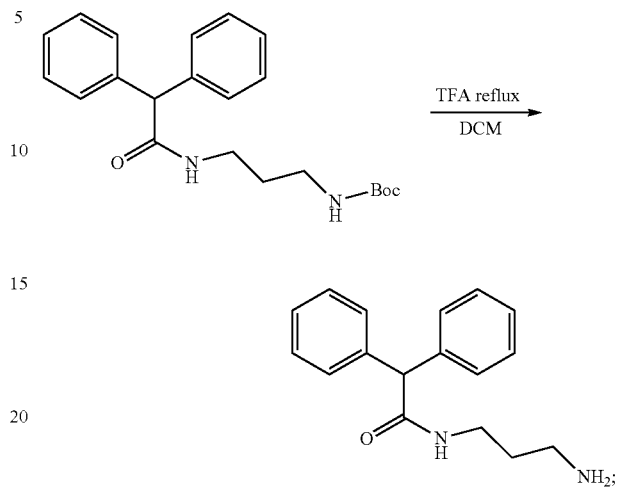

a compound obtained after removing the t-butyloxycarboryl protection performing an amino-ester exchange with 4-quinazolone-2-carboxylic acid ethyl ester to obtain a target compound:

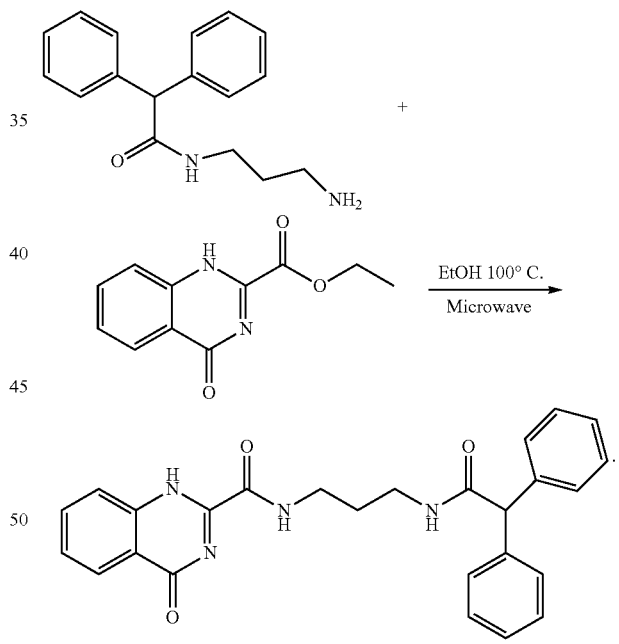

* * * * *